(12) United States Patent
Erickson et al.

(10) Patent No.: US 7,998,180 B2
(45) Date of Patent: Aug. 16, 2011

(54) RADIOLUCENT BONE PLATE SYSTEMS AND METHODS OF USE

(75) Inventors: David Erickson, Memphis, TN (US); Wilder Companioni, Cordova, TN (US); Nelson Oi, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/418,505

(22) Filed: Apr. 28, 2006

(65) Prior Publication Data

US 2007/0270851 A1  Nov. 22, 2007

(51) Int. Cl.
*A61B 17/80* (2006.01)
(52) U.S. Cl. ......... 606/286; 606/280; 606/289; 606/290
(58) Field of Classification Search .................... 606/69, 606/70, 71; 433/172–211
See application file for complete search history.

(56) References Cited

U.S. PATENT DOCUMENTS

| | | | |
|---|---|---|---|
| 5,015,183 A * | 5/1991 | Fenick | 433/76 |
| 5,320,100 A * | 6/1994 | Herweck et al. | 600/431 |
| 5,364,399 A * | 11/1994 | Lowery et al. | 606/69 |
| 5,931,838 A * | 8/1999 | Vito | 606/61 |
| 6,152,927 A * | 11/2000 | Farris et al. | 606/287 |
| 6,342,055 B1 * | 1/2002 | Eisermann et al. | 606/69 |
| 6,423,067 B1 * | 7/2002 | Eisermann | 606/65 |
| 6,723,097 B2 * | 4/2004 | Fraser et al. | 606/61 |
| 2004/0039387 A1 * | 2/2004 | Gause et al. | 606/69 |
| 2004/0127904 A1 * | 7/2004 | Konieczynski et al. | 606/70 |
| 2005/0036945 A1 * | 2/2005 | Thomas et al. | 424/9.4 |
| 2005/0177175 A1 * | 8/2005 | Johnstone | 606/130 |
| 2006/0009770 A1 * | 1/2006 | Speirs et al. | 606/69 |
| 2006/0241400 A1 * | 10/2006 | Bucholz | 600/424 |
| 2006/0241760 A1 * | 10/2006 | Randall et al. | 623/17.11 |
| 2007/0162019 A1 * | 7/2007 | Burns et al. | 606/69 |

* cited by examiner

*Primary Examiner* — Nicholas Woodall (57) ABSTRACT

Apparatus, systems and methods for making, using, implanting, and visualizing portions of a medical implant are provided. One such implant includes a bone plate at least partially of a radiolucent material having at least one aperture, and a fastener at least partially of a radiolucent material to extend through the aperture. The fastener has a distal end and a proximal end, with at least a portion of the proximal end is of a radiopaque material. A fastener lock is included to engage the fastener proximal end to maintain the fastener position relative to the bone plate. At least a portion of the fastener lock is of a radiopaque material. In this manner, at least a portion of the implant is adapted to be visible on a radiographic image.

9 Claims, 6 Drawing Sheets

RADIOLUCENT BONE PLATE SYSTEMS AND METHODS OF USE

BACKGROUND

The present invention relates generally to radiolucent medical implants, and more specifically to radiolucent spinal implants having systems and methods for improved visualization of select components.

Spinal implants are often used in the surgical treatment of spinal disorders such as degenerative disc disease, disc herniations, scoliosis or other curvature abnormalities, and fractures. Many different types of treatments are available. In some cases, dynamic implants are used to preserve motion between vertebral bodies. In other cases, spinal fusion is encouraged to inhibit relative motion between vertebral bodies. Various types of implants may be used, including intervertebral and interspinous implants. Other implants are attached to the exterior of vertebrae, including at a posterior, anterior, or lateral surface of the vertebrae.

Some spinal implants use metal alloys including titanium, and stainless steel. Metals such as these are visible on and/or interfere with or obscure MRI and X-ray images. Non-metallic implant designs may be generally radiolucent and not visible in X-ray imaging. However, X-ray imaging may be desirable during installation of the device and post-operation to check the location and mechanical condition of the implant. It also may be necessary to verify the physical relationship between implant components post operatively, which can be difficult or impossible with radiolucent implants. Improvements are desired.

SUMMARY

The present invention includes apparatus, systems and methods for making, using, implanting, and visualizing portions of a medical implant. Some illustrative embodiments disclosed herein are directed to a surgical implant that includes radiopaque markers or components to permit visualization of the implant on a radiograph. The markers may be of various shapes, materials, or sizes, and may be contained within the implant or located on an outer surface of the implant. The markers may be observed on a radiograph to allow analysis of the position and/or integrity of the implant.

In one embodiment of the present invention, an implant for insertion into a patient includes a bone plate comprising a radiolucent material. The bone plate may be partially, or fully made from the radiolucent material. The bone plate includes at least one aperture, with the implant including a fastener comprising a radiolucent material adapted to extend through the aperture. The fastener has a distal end and a proximal end, with at least a portion of the proximal end comprising a radiopaque material. A fastener lock is included, adapted to engage the fastener proximal end to maintain the fastener position relative to the bone plate. At least a portion of the fastener lock comprises a radiopaque material. In this manner, at least a portion of the implant is adapted to be visible on a radiographic image.

In alternative aspects of the present invention, the implant proximal head includes a radiopaque ring or a radiopaque marker. The radiopaque materials used for the fastener lock and the fastener portion may be different radiopaque materials, or a same radiopaque material. The radiolucent materials of the bone plate and fastener may comprise, in some embodiments, a polymer, a bioresorbable material, or the like.

The present invention also provides for orthopedic implants. In one such embodiment, the implant includes an elongate member having at least one aperture therethrough. The elongate member, which in some embodiments is a bone plate, comprises a radiolucent material. The implant includes a fastener adapted to extend through the aperture to couple the elongate member to a bone. The fastener, which in some embodiments is a bone screw, has a distal end and a proximal end, and comprises a radiolucent material. A radiopaque marker, which in some embodiments is a radiopaque ring, is coupled to the fastener proximal end. A fastener lock comprising a radiopaque material is included. The lock is adapted to lock, fix or couple the fastener proximal end relative to the elongate member.

In some embodiments, the fastener lock and radiopaque marker are visible in a radiograph image. In this manner, the image can be used to verify that the lock and fastener are in the proper orientation. The fastener lock may comprise a locking cap. In some aspects, the locking cap is adapted to at least partially recess in the aperture with the fastener, or in a separate aperture. The fastener lock may engage a side of the fastener proximal end, or a proximal-facing surface of the fastener proximal end. In doing so, in some embodiments the engagement occurs proximal to the radiopaque marker. In this manner, the fastener lock can prevent or help prevent back out of the fastener, and the position of the lock and fastener can be verified on a radiograph notwithstanding the use of radiolucent materials for the elongate member and/or fastener. This feature will be particularly useful where the elongate member is constructed of a material that prevents analysis of the interface between the fastener proximal end and the elongate member absent the radiopaque marker.

The present invention further provides methods of implanting a medical device, such as a bone plate. One such method includes providing a bone plate of radiolucent material, and coupling the bone plate to a bone using a screw. The screw comprises a radiolucent material and a radiopaque marker. The method includes engaging a screw head portion of the screw with a screw lock. The screw lock, or a portion thereof, comprises a radiopaque material. The method further includes imaging the engaged screw and screw lock to determine a relative position of the radiopaque marker and the screw lock. In some aspects, the imaging includes a radiographic imaging.

In some embodiments, the bone plate is a spinal plate coupled to a vertebra. The process of engaging the screw head with the screw lock may comprise, in alternative embodiments, engaging a proximal-facing surface or a side surface of the screw head portion with the screw lock. In some embodiments, a multi-lock is used. For example, the bone plate may be coupled to one or more bones using one or more screws, with the screw lock engaging the screw head portions of two (or more) bone screws. In some aspects, the screw is a non-metallic screw, such as a polymer screw, and the radiopaque marker includes or comprises a radiopaque ring coupled to the screw.

Other features and advantages of the invention will appear from the following description in which the preferred embodiment has been set forth in detail in conjunction with the accompanying drawings.

DETAILED DESCRIPTION

The various embodiments disclosed herein relate to visualization markers and components for medical implants, including spinal implant devices used in the surgical treatment of spinal disorders. Generally, the markers may improve the visibility of the spinal implants in radiograph images, thereby allowing surgeons to check the position or integrity of the spinal implant during and after surgical installation of the implant. The markers may be positioned a known distance apart or at predetermined locations that may be verified through inspection of a radiograph image. In a particular embodiment, the physical relationship between screws, screw locks and plates may be verified through inspection of a radiograph image.

Figure 1:
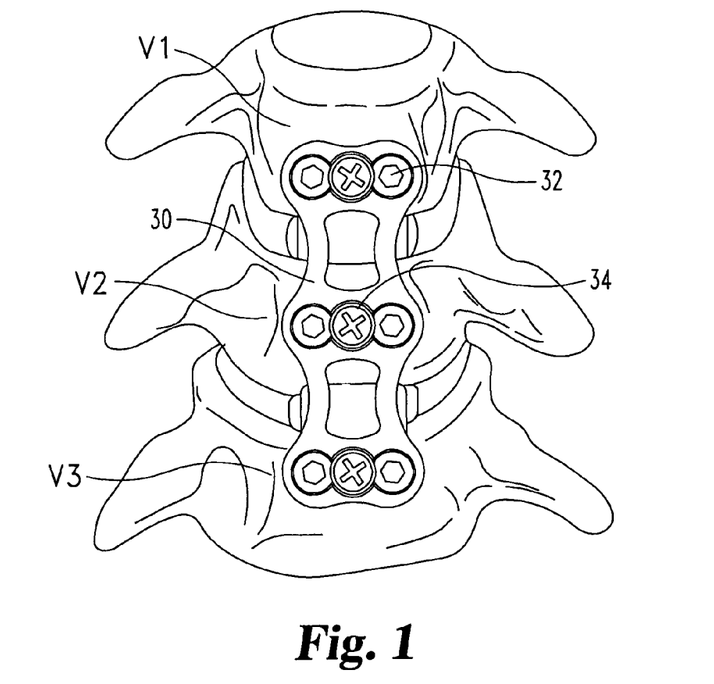
FIG. 1 is a perspective view of a spinal plate secured to vertebral members according an embodiment of the present invention.

Some embodiments of a visualization marker may be employed with a plate 30 as illustrated in FIG. 1. Plate 30 may be secured to a plurality of vertebral members V1, V2, V3 with bone screws 32. Bone screws 32 may be captively secured to plate 30 with one or more retainers 34. In the embodiment shown, plate 30 is coupled to three vertebral members V1, V2, V3. Plates 30 that attach to fewer and more vertebral levels are also contemplated within the scope of the present invention. In one embodiment, plate 30 is a cervical plate, although plate 30 also may couple to vertebral members in the thoracic, lumbar and/or sacrum regions of the spine. In one embodiment, plate 30 is an anterior plate. In other embodiments, plate 30 may be attached to a lateral or posterior side of vertebral members or the skull (not shown).

In some embodiments, plate 30 may be constructed of an implantable grade, non-metallic material, such as a resin or polymer. Some non-limiting examples of materials that may be used for implants according to the present invention, such as plate 30, include polyethylene, polypropylene, nylon, polyether-ether-ketone (PEEK), polyether ketone (PEK), polyether ketone ketone (PEKK), and polaryl ether ketones (PAEK). Implants 30 may be constructed of other copolymers or compounds that include bioresorbable materials such as PLA (poly-lactic acid), PGA (poly-glycolic acid), PCL (poly-caprolactone), and PLDLA (70% poly (L-lactide)30% poly (D, L-lactide), which is available under the trade name Hydrosorb™ from MacroPore Biosurgery in San Diego, Calif., USA. In various formulations, materials such as these may be radiolucent, which generally refers to that characteristic which prevents the material from appearing in radiographic images (e.g., plain film, CT scan, fluoroscopy) when implanted within a patient. Accordingly, the spinal implants of the present invention may include one or more radiopaque markers or components to make at least a portion of the implants visible in radiograph images.

Various biocompatible metals, including stainless steel, titanium, gold, tantalum and platinum may be used to create marking pins, wires, spheres or other shapes as radiograph markers to indicate the position of implant 30 or portions thereof. In other embodiments, the radiopaque markers are comprised of a radiolucent material that is impregnated or coated with a radiopaque substance such as barium sulfate or bismuth subcarbonate compounds. The markers may be constructed with different shapes, including for example spherical, cylindrical, oblong, or other shapes that describe the geometry being radiographed. Furthermore, the markers may have different cross sections, including for example circular, oval, square, triangular, or elliptical shapes. The markers may be incorporated into implants 30 using a variety of techniques. For example, the markers may be bonded in place, molded into the implant, or press fit into machined apertures (not explicitly shown) in the implant.

Figure 2:
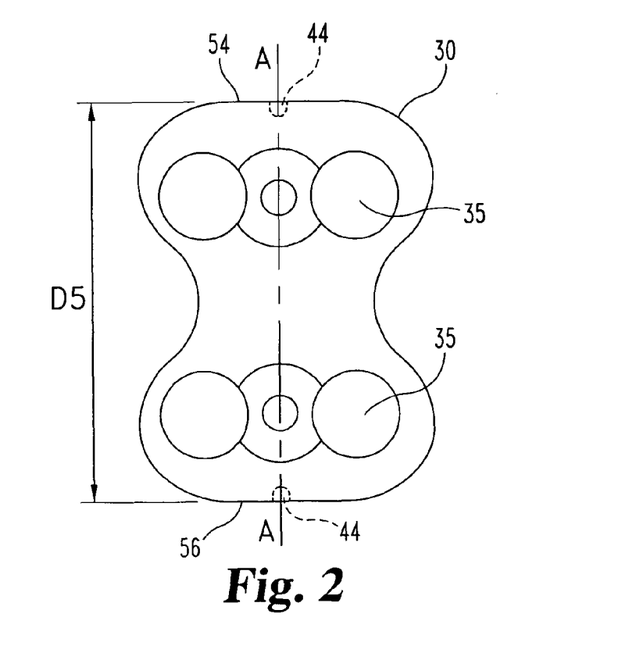
FIG. 2 is a frontal view of a spinal plate having visualization markers according to an embodiment of the present invention.
Figure 3:
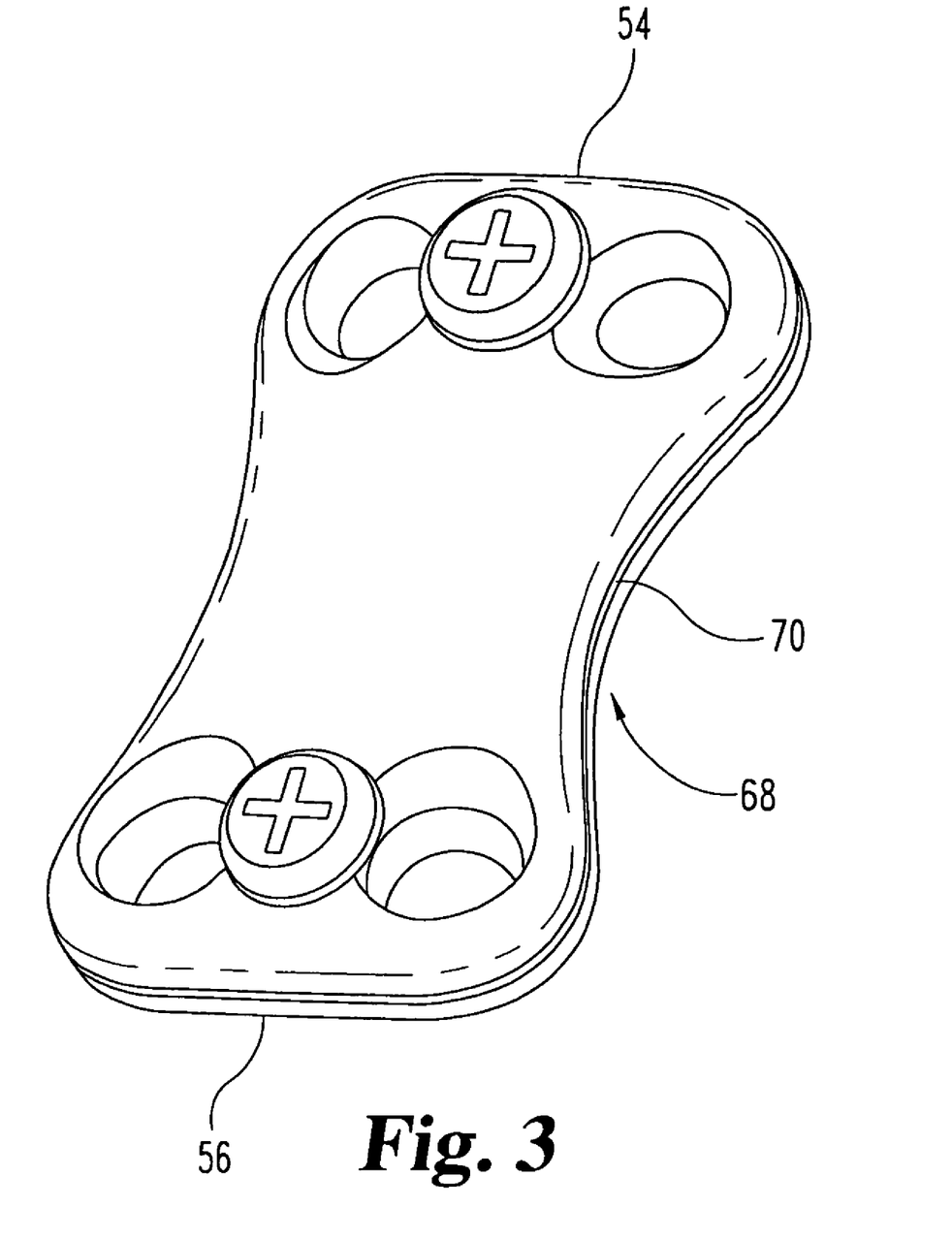
FIG. 3 is a perspective view of a spinal plate having visualization coatings according to an embodiment of the present invention.

FIG. 2 shows a representative plate 30 incorporating a plurality of markers 44. Plate 30 also comprises a plurality of apertures 35 through which bone screws or other fasteners 32 are inserted to secure plate 30 to vertebral members V1, V2. Tension, compression, and torsion loads may be applied to plate 30, particularly around and between apertures 35. In the embodiment shown, markers 44 are disposed at opposite longitudinal ends 54,56 of plate 30, and are therefore separated by approximately the distance D5. While the illustrated markers 44 are aligned with a central longitudinal axis A, in other embodiments they fall on opposite sides or a same side of axis A. Plate deformations, including elongation, bending, or twisting may be verified post-surgery using a radiograph to verify the position of markers 44 as well as the distance between markers 44. FIG. 3 shows another embodiment of plate 30 with a radiopaque coating or layer 70 disposed about a periphery 68 of plate 30, or a portion of periphery 68. In some embodiments, various markers 44 or components can be distinguished from one another in a radiograph by using different concentrations of a radiopaque material, different types of radiopaque materials, different compositions, materials, size, shape or the like.

In some embodiments of the various implants 30, markers 44 are disposed interior to the outer surface of implant 30. Alternatively, radiopaque markers 44 may be attached to implant 30 through bonding, heating, ultrasonic welding or other process capable of attaching markers 44 to implant 30. In still other embodiments, a radiopaque coating is used. The coating may comprise a biocompatible compound that includes a radiopaque filler, such as metal particles, barium sulfate, or bismuth subcarbonate. The coating may be applied as a secondary process after the implant 30 is manufactured. Alternatively, the coating may be molded into implant 30 or a component thereof.

Figure 4:
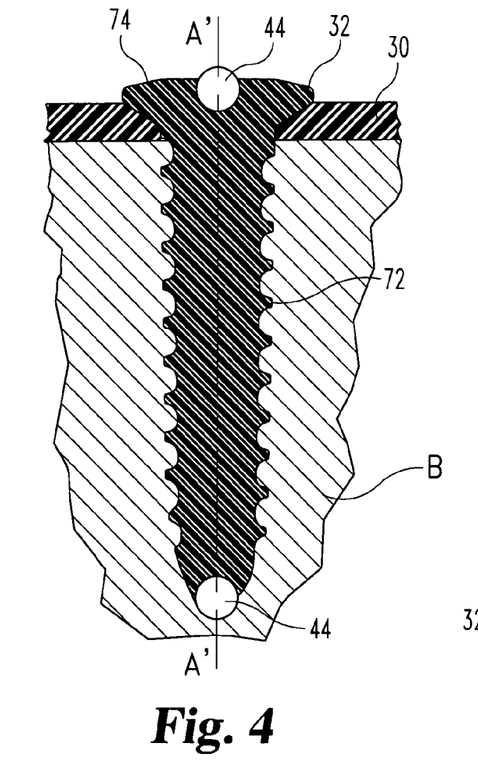
FIG. 4 is a cross sectional view of a bone screw and spinal plate having visualization markers according to an embodiment of the present invention.

Radiopaque markers may be incorporated into or used in conjunction with other spinal implants, including the various components thereof For example, FIG. 4 shows a cross section view of a plate 30 secured to a bony member (e.g., vertebra) B by a bone screw 32. The bone screw 32 comprises a threaded portion 72, having a length T, for engagement and retention in the bony member B. The bone screw 32 further comprises an enlarged head 74 that compresses the plate 30 into contact with the bony member B. The illustrated bone screw 32 may be radiolucent. Accordingly, radiopaque markers 44 are incorporated into the longitudinal ends of the bone screw 32.

Figure 5:
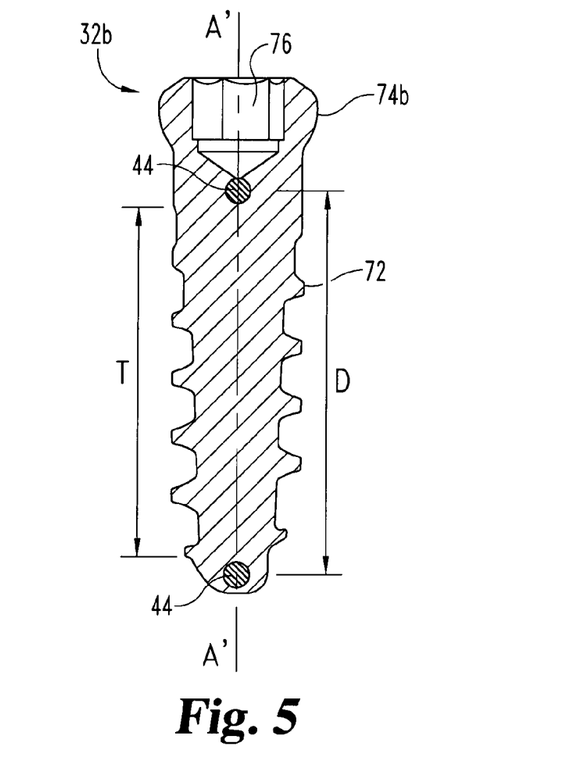
FIG. 5 is a cross sectional view of a bone screw according to another embodiment of the present invention.

FIG. 5 shows an embodiment of a bone screw 32b in which radiopaque markers 44 are disposed. In this exemplary embodiment, the markers 44 are disposed near the head 74b and at the opposite longitudinal end toward the end of the threaded portion 72. The markers 44 may be aligned with the central longitudinal axis A' of the bone screw 32b. The markers 44 may be spaced apart a distance D13 that is substantially the entire length of the bone screw 32b. One marker 44 may be positioned at the bottom of a recessed driving feature 76 in the screw head portion 74b. Driving feature 76 may be a hex recess or other type of recess adapted to accept a driver tool, including but not limited to slotted, Torx, cross, square, and spline shaped driving features 76. Driving feature 76 may be aligned with a longitudinal axis A' of bone screws 32a, 32b. The distance D between the markers 44 may be greater than, less than, or equal to the length T of the threaded portion 72 of the bone screw 32b.

Turning now to FIGS. 6-9B, an implantable system 100 of the present invention will be described. In a particular embodiment, system 100 includes a bone plate 110, as may be used to facilitate fusion between or provide stability to two or more adjacent vertebral bodies. In a particular embodiment, plate 110 is made from or partially comprises a radiolucent material. The materials used may include those listed elsewhere herein. Plate 110 has an upper surface 112 and a lower surface 114 defining a plate thickness therebetween. Plate 110 includes a plurality of apertures 116, with at least some apertures adapted to receive a fastener therethrough for coupling plate 110 to the vertebral bodies. In some embodiments, the fasteners may be fixed angle bone screws, variable angle bone screws, cannulated screws, or the like. In the depicted embodiment, plate 110 also includes one or more additional apertures 120 positioned generally between apertures 116. Apertures 120 may, for example, be used by the surgeon to view the disc space between the vertebral bodies to which plate 110 is attached. Apertures 120 also may provide a location by which an instrument, such as a plate holder, can engage plate 110 during surgery.

Figure 6:
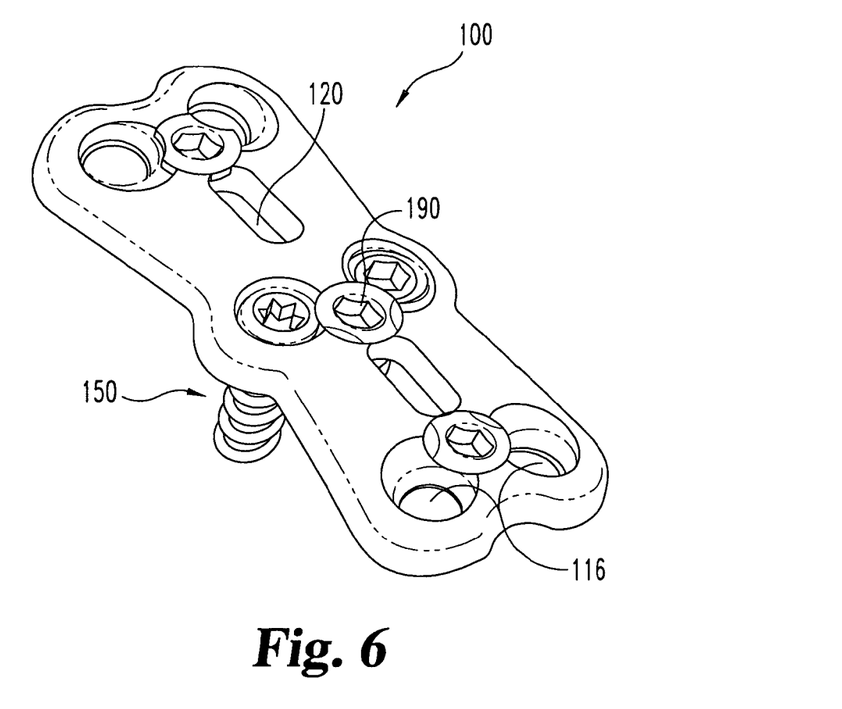
FIG. 6 is an overall view of an implant according to an embodiment of the present invention.

As known to those skilled in the art, bone screws can potentially back out from the bone into which they are screwed. Thus, plate 110 includes a bone screw locking mechanism 190 adapted to limit or prevent bone screws from backing out of plate 110. In one embodiment, locking mechanism 190 is disposed within an aperture 130. Aperture 130 may extend part way or completely through plate 110. In one embodiment, aperture 130 is positioned along the longitudinal axis or midline of plate 110. In this manner, locking mechanism 190 disposed in aperture 130 is also positioned along the longitudinal axis or midline of plate 110. In an alternative embodiment, locking mechanism 190 is a single lock mechanism for locking a single fastener relative to bone plate 110. Such a locking mechanism, in some embodiments, is disposed at least partially in aperture 116 containing the fastener to be locked.

Figure 7:
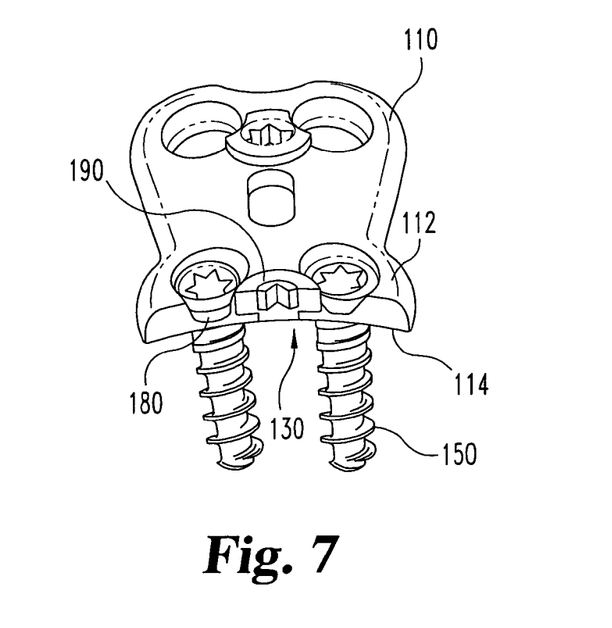
FIG. 7 is an overall view of a portion of the implant shown in FIG. 6.

As shown in FIGS. 6 and 7, in one embodiment locking mechanism 190 comprises a locking cap 190. Locking cap 190 is shown locking two adjacent bone screws disposed through two adjacent apertures 116. In a particular embodiment, locking mechanism 190 comprises a radiopaque material, visible on radiographs, x-rays, or the like. In an alternative embodiment, a portion of locking, cap 190 comprises a radiopaque material.

Figure 8A:
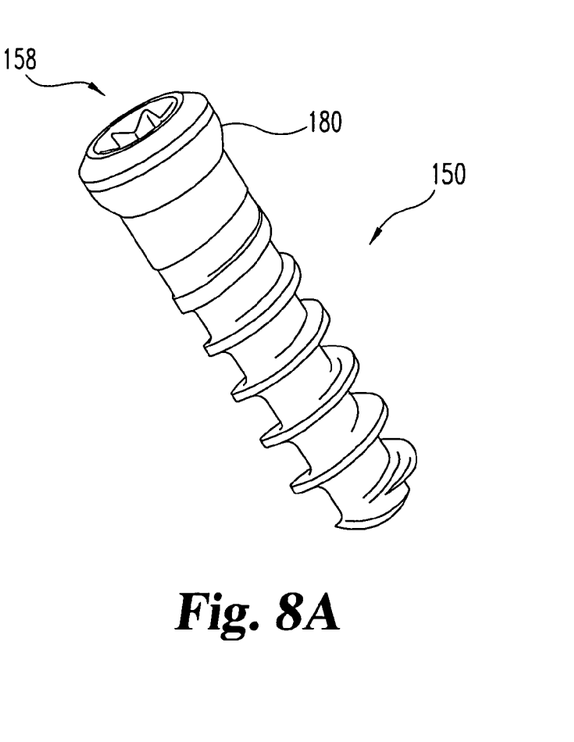
FIGS. 8A and 8B are overall views of a bone screw according to embodiments of the present invention.
Figure 8B:
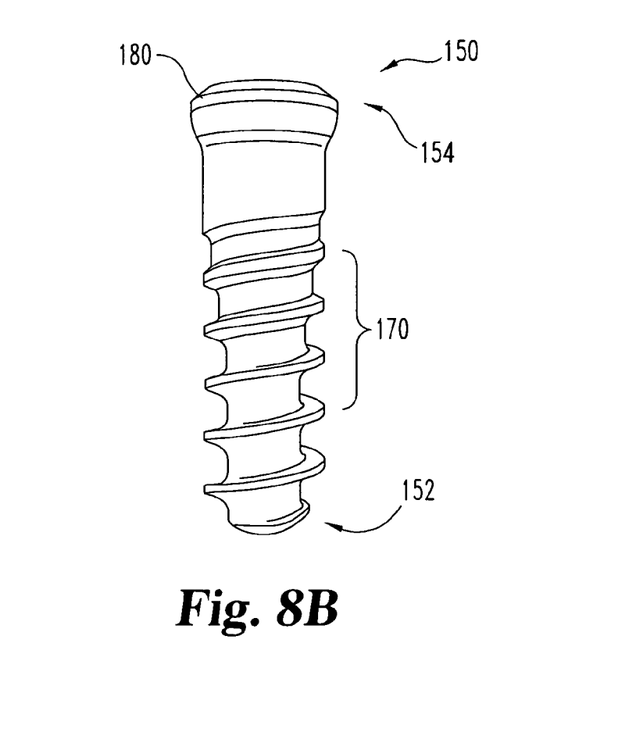

Plate 110 is coupled to bones, such as vertebral bodies, using one or more bone screws 150. As seen in FIGS. 7, 8A and 8B, in one embodiment bone screw 150 has a distal end 152 and a proximal end 154. Proximal end 154 includes a means for coupling a tool or instrument to proximal end 154. This may include, for example, a driving feature 158 similar to driving feature 76 (FIG. 5), a detent, or another mechanism at proximal end 154. Bone screw 150 further includes a threaded region 170 which extends along the full or a partial length of bone screw 150 between ends 152, 154. In a particular embodiment, bone screw 150 comprises a radiolucent material. Such a bone screw 150 may be desirable, for example, to reduce or minimize the likelihood that screw 150 would interfere with a radiograph, x-ray or the like of the patient anatomy into which plate 110 has been implanted.

Using radiolucent plates 110 and screws 150, the surgeon, physician, radiologist, or the like, are able to more easily see the surgical site post-operatively. However, it can be difficult on a radiograph to determine whether the bone screw and locking mechanism 190 have properly engaged to prevent or help prevent back out of screw 150. Thus, in some embodiments, bone screw 150 includes a radiopaque portion 180, which is visible on a radiograph. In a particular embodiment, radiopaque portion 180 comprises a ring of radiopaque material disposed generally around the periphery of proximal end 154, as can be seen in FIGS. 8A-8B. For example, radiopaque portion 180 may be a metal ring disposed around the perimeter of, or adjacent to proximal end 154. In alternative embodiments, radiopaque portion 180 is a radiopaque coating, or other radiopaque marker as described in conjunction with earlier embodiments. Further, while depicted generally as a complete ring, in some embodiments radiopaque portion 180 extends only part of the way around the screw proximal end 154.

Similarly, in some embodiments locking mechanism 190 generally comprises a radiopaque material, such as a metal. As a result, a portion of screw 150 and locking mechanism 190 are visible on a radiograph, x-ray or the like, even when plate 110 and the remaining portions of screw 150 are radiolucent. The ability to see select portions of components within system 100 may allow the surgeon to verify post-operatively that bone screw 150 and locking mechanism 190 are correctly positioned.

Figure 9A:
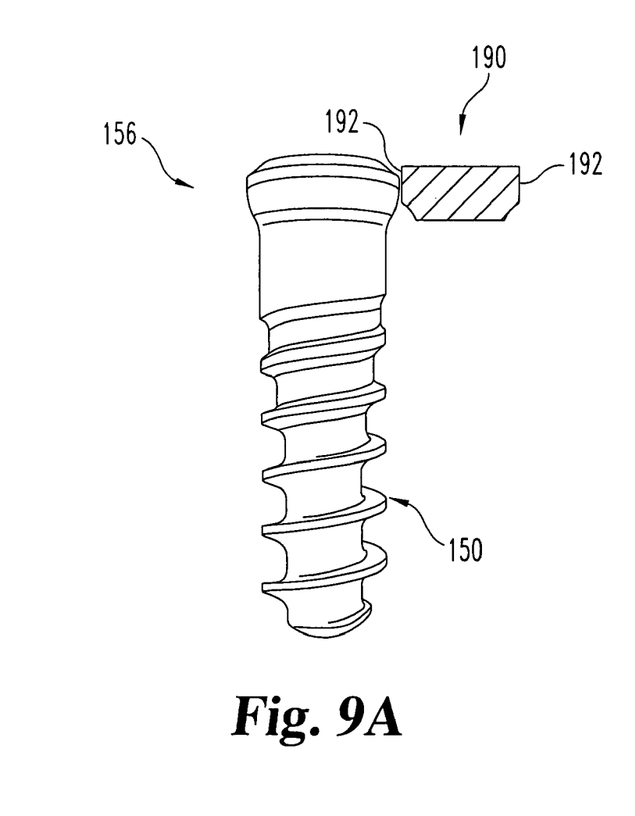
FIGS. 9A and 9B are simplified cross sectional views of portions of bone plate systems according to embodiments of the present invention.

Turning to FIG. 9A, the interface between locking mechanism 190 and bone screw 150 will be further described. In the embodiment shown in FIG. 9A, a side 192 of locking mechanism 190 engages a side 156 of screw proximal end 154. This may occur, for example, using a frictional engagement between sides 192, 156 to prevent rotation of bone screw 150. In a particular embodiment, side 192 may have an irregular or concave shape which couples or mates with a convex or curved screw side 156.

Figure 9B:
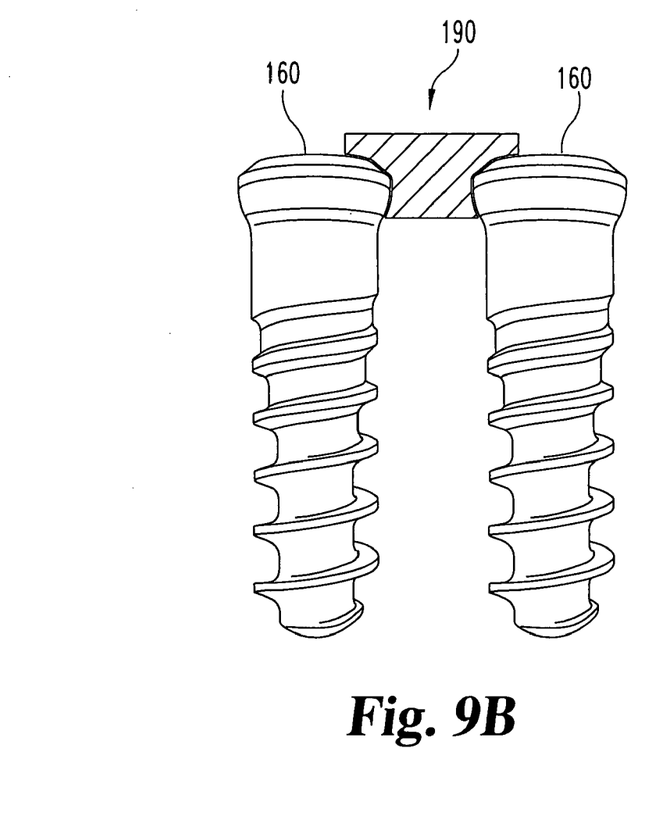

In an alternative embodiment shown in FIG. 9B, locking mechanism 190 overlaps or overhangs a portion of aperture 116 and/or a proximal-facing surface 160 of bone screw 150. In this embodiment, side 192 of locking mechanism 190 may have alternative shapes, provided at least a portion of mechanism 190 overhangs or extends into aperture 116 and/or over surface 160. Locking mechanism 190 in this embodiment is shown engaging two adjacent screws 150, although in alternative embodiments it can engage a single screw 150, or more than two screws 150.

In some embodiments, locking mechanism 190 comprises a radiopaque material. In this manner, a radiograph image will depict the location of locking mechanism 190 and the location of the radiopaque portion of screw 150. The relationship between the two components can be verified using the radiograph. This may be particularly useful, for example, to confirm that screw 150 and locking mechanism 190 are properly positioned to prevent back out or other undesired movements of screw 150.

In alternative embodiments, locking mechanism 190 generally comprises a radiolucent material, with locking mechanism 190 having a radiopaque portion, or a radiopaque component coupled thereto. For example, locking mechanism 190 may include a radiopaque ring such as a metal ring. This radiopaque ring may be coupled to a desired portion of locking mechanism 190 to facilitate viewing on a radiograph relative to bone screw 150. For example, in the embodiment shown in FIG. 9B, the portion of locking mechanism 190 which overhangs screw surface 160 may be the radiopaque portion visible on a radiograph image. In, this manner, the image can be used to verify that locking mechanism 190 overhangs screw surface 160. Alternatively, a radiopaque coating may be applied to the desired portion of locking mechanism 190, and/or screw 150, to facilitate imaging.

Spatially relative terms such as "under", "lower", "over", "upper", "top", "bottom" and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

Components of the described embodiments may be made from a variety of materials compatible for use with the human body, including without limitation metals (e.g., titanium, nitinol, stainless steel), ceramics, polyethylene, PEEK, and other materials.

Having described several embodiments, it will be recognized by those skilled in the art that various modifications, alternative constructions, and equivalents may be used without departing from the spirit of the invention. Accordingly, the above description should not be taken as limiting of the scope of the present invention.

What is claimed is:

1. An orthopedic implant, comprising:
    an elongate member having at least one aperture therethrough, the elongate member comprising a radiolucent material;
    a fastener having a central longitudinal axis adapted to extend through the aperture to couple the elongate member to a bone, the fastener having a tip for connection to bone and a head, the fastener comprising a radiolucent material;
    a first radiopaque marker coupled to the fastener head, said first radiopaque marker being partially buried in said head and partially exposed and extending a distance above said head, so that said first radiopaque marker is observable both radiographically and by the naked eye;
    a second radiopaque marker coupled to the fastener tip, said second radiopaque marker being partially buried in said tip and partially exposed and extending a distance beyond the end of said tip; and
    a fastener lock comprising a radiopaque material, the fastener lock adapted to lock the fastener head relative to the elongate member, and the fastener lock being non-concentric with said longitudinal axis,
    wherein the first radiopaque marker and the second radiopaque marker are disposed in a configuration with the fastener such that orientation and positioning of the fastener and the fastener lock are verifiable radiographically.

2. The implant as in claim 1 wherein the elongate member comprises a bone plate.

3. The implant as in claim 2 herein the bone plate radiolucent material comprises a polymer.

4. The implant as in claim 1 wherein the fastener comprises a bone screw.

5. The implant as in claim 1 wherein the fastener lock comprises a locking cap, the locking cap adapted to at least partially recess in the at least one aperture.

6. The implant as in claim 1 wherein the fastener lock comprises a locking cap, the locking cap adapted to at least partially recess in a second aperture in the elongate member.

7. The implant as in claim 1 wherein the fastener lock is adapted to engage a lateral side of the fastener proximal end.

8. The implant as in claim 1 wherein the fastener lock is adapted to engage a proximal-facing surface of the fastener proximal end.

9. A method of implanting an orthopedic implant with bone, the method comprising the steps of:
    providing an orthopedic implant, the orthopedic implant including:
    a radiolucent, elongate member having at least one aperture,
    a radiolucent fastener having a central longitudinal axis and being adapted to extend through the aperture to couple the elongate member with bone, the fastener including a head and a tip,
    a first radiopaque marker disposed with the head and extending a distance above the head,
    a second radiopaque marker disposed with the tip and extending a distance beyond the tip, and
    a radiopaque fastener lock adapted to lock the head relative to the elongate member and being non-concentric with the central longitudinal axis;
    coupling the elongate member to bone with the fastener;
    engaging the radiopaque fastener lock with the fastener; and
    verifying radiographically the orientation and positioning of the fastener and the radiopaque fastener lock based on the configuration of the first radiopaque marker and the second radiopaque marker with the fastener.

* * * * *